United States Patent [19]

Muchow et al.

[11] Patent Number: 5,350,580
[45] Date of Patent: Sep. 27, 1994

[54] DEVICE AND METHOD FOR EXTENDED DELIVERY OF PHARMACOLOGICALLY ACTIVE AGENTS TO THE EAR

[75] Inventors: David C. Muchow, Transit Township, Sibley County; Larry M. Sirvio, Cottage Grove, both of Minn.

[73] Assignee: Minnesota Mining and Manufacturing Company, St. Paul, Minn.

[21] Appl. No.: 24,191

[22] Filed: Feb. 26, 1993

Related U.S. Application Data

[63] Continuation of Ser. No. 770,708, Oct. 3, 1991, abandoned, which is a continuation of Ser. No. 683,099, Apr. 10, 1991, abandoned, which is a continuation of Ser. No. 488,650, Mar. 5, 1990, abandoned.

[51] Int. Cl.$^5$ .............................................. A61F 9/02
[52] U.S. Cl. .................................. 424/437; 424/422; 514/956
[58] Field of Search .................. 424/437, 422; 514/956

[56] References Cited

U.S. PATENT DOCUMENTS

| | | | |
|---|---|---|---|
| 3,887,699 | 6/1975 | Yolles | 424/19 |
| 4,343,931 | 8/1982 | Barrows | 528/291 |
| 4,367,741 | 1/1983 | Michaels | 128/260 |
| 4,455,144 | 6/1984 | Michaels | 604/892 |
| 4,601,513 | 7/1986 | Cardinal | 424/15 |
| 4,851,513 | 7/1990 | Devore et al. | 530/356 |
| 5,062,829 | 11/1991 | Pryor et al. | 604/57 |

FOREIGN PATENT DOCUMENTS

| | | | |
|---|---|---|---|
| 0025698 | 11/1980 | European Pat. Off. | A61K 9/22 |
| 0257369 | 4/1987 | European Pat. Off. | A61K 9/22 |
| 0311065 | 10/1988 | European Pat. Off. | A61K 9/22 |
| 3617400 | 11/1987 | Fed. Rep. of Germany . | |
| WO89/04674 | 6/1989 | PCT Int'l Appl. | A61L 27/00 |

OTHER PUBLICATIONS

Goodson, et al., *J. Periodontol.*, 54:575-579 (1983).
D. Cohn, et al., *Polymer*, 28:2018 (1987).
E. Nyilas, et al., *Trans. Soc. Biomat.*, 6:84 (1983).
Cohn, et al., *J. Biomed. Mat. Res.*, 22:993-1009 (1988).
T. Barrows, *Clin. Mat.*, 1:233-257 (1986).

*Primary Examiner*—D. Gabrielle Phelan
*Attorney, Agent, or Firm*—Gary L. Griswold; Walter N. Kirn; Paul W. Busse

[57] ABSTRACT

A device useful for the treatment of infections of the middle ear in a prophylactic manner. A preferred device involves the use of a biodegradable support incorporating a therapeutically active agent, such as a drug. The device can be surgically inserted into the middle ear and there expand in order to substantially contact the walls of the middle ear. As it biodegrades, the expanded device provides prolonged, responsive release of active agent to the middle ear.

5 Claims, 2 Drawing Sheets

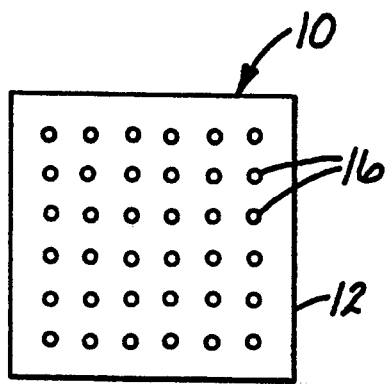
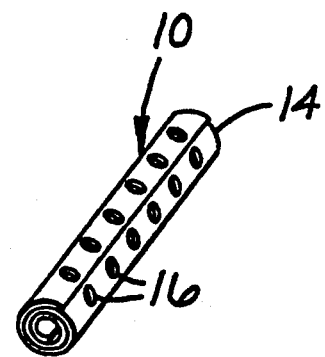
Fig 1A  Fig 1B
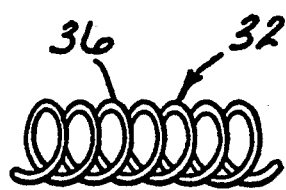
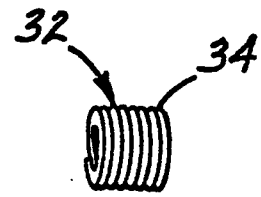
Fig 4A  Fig 4B

DEVICE AND METHOD FOR EXTENDED DELIVERY OF PHARMACOLOGICALLY ACTIVE AGENTS TO THE EAR

This application is a continuation of U.S. application Ser. No. 07/770,708 filed Oct. 3, 1991, now abandoned, which is a continuation of U.S. application Ser. No. 07/683,099 filed Apr. 10, 1991, now abandoned, which is a continuation of U.S. application Ser. No. 07/488,650 filed Mar. 5, 1990, now abandoned.

TECHNICAL FIELD

The present invention relates to methods and compositions useful for treating middle ear infections. In another aspect the invention relates to methods and compositions useful for delivering pharmacologically active agents, including drugs such as antibiotics, to the middle and/or inner ear in order to treat infections, particularly in a prophylactic manner.

BACKGROUND OF THE INVENTION

Otitis media is a term used to describe infections of the middle ear, which infections are very common, particularly in children. In children, the disease is most often associated with upper respiratory afflictions which trigger a transudate secretion response in the Eustachian tube and middle ear. Because of the immature anatomy of the child's skull (usually through about the age of 9), bacteria and viruses easily migrate from the naso-pharynx to the middle ear via the Eustachian tube. These events can cause the Eustachian tube to become blocked, preventing ventilation (pressure equilibration) and drainage of the middle ear.

In its more severe forms, where purulent exudate is formed in the middle ear, toxins and an abundance of endogenous anti-microbial enzymes can cause irreparable damage to sensory-neural and sound conducting structures. Recent research even suggests that many of the middle and inner ear diseases that are seen in adult patients can be attributed to a frequent and severe incidence of otitis in childhood. For this reason physicians are increasingly using antibiotics and ventilation devices prophylactically. It is estimated that over 1 billion dollars are spent annually in the United States on the treatment and prevention of otitis media. It has also been estimated that nearly 95% of all children experience one or more episodes of otitis by age 9, and that about 15% of all visits by children to pediatricians are in regard to otitis media.

Current methods of treatment generally involve the systemic use of antibiotics; the use of antibiotic-containing ear drops; and/or, particularly in more chronic cases, the insertion of a myringotomy tube through a small incision in the eardrum, in order to provide ventilation and allow drainage of the middle ear cavity over an extended period of time.

Myringotomy tubes however carry associated risks, e.g., of becoming plugged, falling out, or themselves providing an additional route for infection of the middle ear.

The effectiveness of antibiotic therapy for the middle ear is hampered by the routes of administration currently available. Typically antibiotics are systemically administered for infections of the middle ear, e.g., in a responsive or prophylactic manner. Systemic administration of antibiotics to combat middle ear infection generally results in a prolonged lag time to achieve therapeutic levels in the middle ear, and requires high initial doses in order to achieve such levels. These drawbacks complicate the ability to obtain therapeutic levels and may preclude the use of some antibiotics altogether. Systemic administration is most often effective when the infection has reached advanced stages, but at this point permanent damage may already have been done to the middle and inner ear structure.

Drugs also can be administered by injection or lavage to the middle ear, but such administration cannot generally be used to achieve prolonged therapeutic levels of antibiotic. Similarly ear drops can be used to apply antibiotics to the ear canal, but the ability of antibiotics to reach the middle ear when applied in this manner is difficult to predict or control, and carries questions, e.g., regarding the possible ototoxic effects of penetration enhancers that may be used. Middle ear drug delivery is further complicated by the fact that the ciliary action of the cells lining the mucous membrane has the effect of clearing the middle ear of medications that do arrive.

In one approach, German Patent No. DE 3,617,400 describes a method of injecting aerosol into the middle ear via the Eustachian tube. The aerosol is administered at the moment the patient swallows, which causes the Eustachian tube to open. Also U.S. Pat. Nos. 4,367,741 and 4,455,144 describe flexible walled dispensers which can be used to administer drug into a number of body cavities, including ear and ocular applications.

Clearly what is needed is a means to deliver therapeutically effective levels of drug to sufferers of chronic and recurrent otitis, and other diseases of the middle and/or inner ear, in a fashion that is prompt, responsive, prolonged, effective, and safe.

SUMMARY OF THE INVENTION

The present invention provides a device incorporating one or more pharmacologically active agents, the device being particularly useful for treating middle ear infections in a prophylactic manner. The device comprises a biodegradable support incorporating a therapeutically effective releasable amount of at least one such active agent, the characteristics of the device being such that (1) the device is provided retained or retainable in an insertable shape of initial dimensions that allow it to be surgically inserted into the middle ear; (2) upon insertion into the middle ear, the device is capable of expanding towards its original shape in order to provide a surface that substantially contacts the walls of the middle ear without substantially occluding the middle ear space; and (3) once expanded, the device is capable of providing extended release of active agent to the middle ear.

A preferred device is in the form of an antibiotic-impregnated, perforated sheet of biodegradable polymeric support material having initial dimensions of on the order of 1 cm × 1 cm in size. The sheet is provided rolled into the insertable shape of a tube having a diameter of about 2 mm, and is retained in such shape by means of an added, dissolvable retaining gel. A device having such a shape can be easily inserted into the middle ear, such as through the same type of surgical incision used to insert a myringotomy tube.

Once in the middle ear, the retaining gel dissolves away upon contact with the environment of the middle ear, allowing the device to tend towards its original sheet-like shape. The device thereby partially unrolls, e.g., into a generally cylindrical shape. In its partially unrolled shape it is held in situ by the walls of the middle ear. The exterior surface of the resultant cylindrical shape substantially contacts the walls of the middle ear.

Thereafter the antibiotic is slowly released from the device, e.g., over a period of one or more months. Although not meaning to be bound by theory, the antibiotic is believed to be released in a number of ways, e.g., by diffusion at areas of contact between the device and walls of the middle ear; by leaching from the device into effusions present in the middle ear; and by release of antibiotic in the course of degradation of the support itself.

A preferred device of the present invention is particularly useful for prophylactic drug applications, since the level of drug released can be responsive to the presence of infection. Where no infection exists, and no effusion therefore exists in the middle ear, drug release will be minimal, e.g., due mostly to contact with the walls of the middle ear and degradation of the support. When a recurrent infection becomes active again, resulting in fluid buildup in the middle ear, the fluid will serve to enhance the leaching of drug from the support in order to provide immediate, increased, and prolonged delivery of the drug directly in the area of infection. As a result, the drug or other active agent is better able to concentrate and be effective in the middle ear and communicating structures than is a drug that is administered systemically in a prophylactic manner.

The device of the present invention is useful for treating infections and other diseases of the middle ear. It also is useful for treating infections of the inner ear, e.g., when used with active agents that are able to cross the round window membrane separating the middle from the inner ear.

In another aspect, the present invention provides a method of treating middle ear infections by the use of a device as described herein.

BRIEF DESCRIPTION OF THE DRAWING

FIG. 1 illustrates a preferred device of the present invention, including both an elevational view of the device in its unrolled form (1A) and an isometric view of the same device in its rolled form (1B).

FIG. 4 illustrates isometric views of an alternative embodiment of the device of the present invention in both its uncoiled (4A) and coiled (4B) forms.

DETAILED DESCRIPTION OF THE INVENTION

Figure 2:
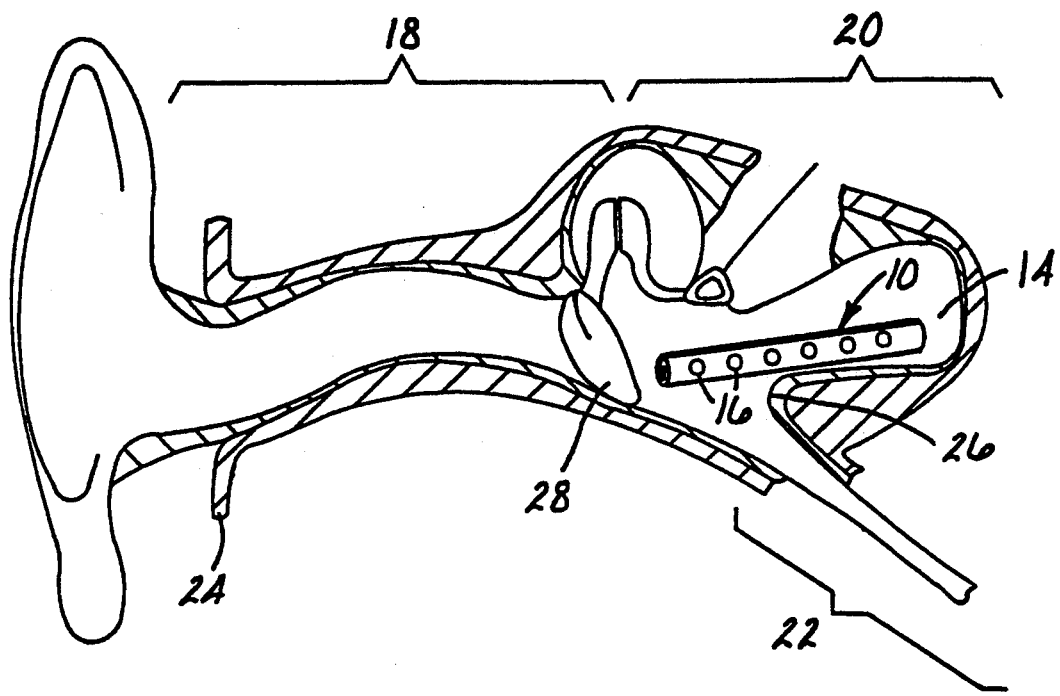
FIG. 2 illustrates a cross-sectional view of the ear, showing the device of FIG. 1B immediately after insertion and placement in the middle ear.

The present invention provides a device incorporating one or more pharmacologically active agents such as drugs, the device being particularly useful for treating middle ear infections in a prophylactic manner. The device comprises a biodegradable support incorporating a therapeutically effective releasable amount of at least one such active agent, the characteristics of the device being such that (1) the device is provided retained or retainable in an insertable shape of initial dimensions that allow it to be surgically inserted into the middle ear; (2) upon insertion into the middle ear, the device is capable of expanding towards its original shape in order to provide a surface that substantially contacts the walls of the middle ear without substantially occluding the middle ear space; and (3) once expanded, the device is capable of providing extended release of the drug to the middle ear.

Preferably the device is retained in its insertable shape by retaining means, e.g., by the use of a gel that dissolves away once inside the middle ear, thereby allowing the support to expand.

With preferred devices; (1) the devices do not substantially occlude the middle ear space, i.e., air and fluid in the middle ear are able to pass through and/or around the expanded device in a substantially unobstructed manner; (2) normal physiological processes, such as long and short term hearing, are not detrimentally affected; (3) active agent is delivered more effectively to the area of the middle ear where the infection occurs and where transudates are produced, yet active agent is able to diffuse to more remote cavities of the middle ear (such as the mastoid), thereby preventing the occurrence of focal areas of infection; (4) the patency of the middle ear is preserved; and (5) the device is located a suitable distance from the ossicular chain, thus precluding the possibility of mechanical interference.

As used herein, the word "device" shall refer to a support incorporating therapeutically active agent. Supports useful for preparing a device of the present invention provide an optimal combination of such properties as an ability to be fabricated into a desired shape, an ability to be loaded with the desired level of active agent in order to achieve a desired release profile, chemical compatibility with the active agent, rate of biodegradation, biocompatibility, hydrophilicity, surface wettability, initial hydration, and controllable swellability.

Examples of suitable materials for use as supports are polymers, including polyesteramides, as disclosed in U.S. Pat. No. 4,343,931, the disclosure of which is incorporated herein by reference, as well as biodegradable polymers and copolymers as described in Cohn, et al., *Polymer*, 28:2018 (1987) and Cohn, et al., *J. Biomed. Mat. Res.*, 22:993–1009 (1988), the disclosures of both of which are incorporated herein by reference. Examples of suitable biodegradable polymers include polyglycolic acid, polylactic acid, copolymers of glycolide and lactide, polyvinyl alcohol, and copolymers of polyethylene oxide and polylactic acid. Other examples of suitable materials for use as the support of the device of the present invention include collagen compounds such as the chemically-modified collagen compounds described in U.S. Pat. No. 4,851,513, the disclosure of which is incorporated herein by reference.

Other suitable materials will be identifiable by those skilled in the art given the present disclosure, such as from among bioabsorbable polymers described by T. Barrows, *Clin. Mat.*, 1:233–257 (1986) and references cited therein, the disclosure of which is hereby incorporated by reference.

Preferred supports exhibit a suitable combination of such properties as biodegradability and hydrophilicity, and mechanical properties, such as flexibility and tensile strength. Particularly preferred are supports that can be fabricated into shapes that uncoil or otherwise expand in the presence of moisture. Although biodegradable supports are particularly preferred, non-degradable supports can be used and later removed from the middle ear, e.g., by tympanotomy. The word "biodegradable", as used herein, refers to a support that degrades over the intended period of use of the device in a manner that results in the release of active agent and the clearing of degradation products from the middle ear, e.g., via the Eustachian tube and cellular clearance.

Examples of preferred materials for preparing supports include polylactic acid, as well as polylactic acid that has been plasticized, e.g., with triethyl citrate, in order to increase suppleness, as described by E. Nylas, et al., *Trans. Soc. Biomat.*, 6:84 (1984) the disclosure of which is incorporated herein by reference.

A device of the present invention can be fabricated into any suitable shape that allows the device to be inserted into the middle ear, with minimal trauma to the eardrum, and there expand in order to substantially contact and be held in place by the walls of the middle ear. For instance, the device can be either inherently small and then expand (e.g., swell) in situ (i.e., once in place in the middle ear), or preferably, the device is inherently larger but temporarily retained (e.g., coiled, rolled, folded, or tied) in smaller, insertable dimensions, e.g., by the use of retaining means as described more fully below.

The word "expand" and inflections thereof, as used herein, refers to an increase in the overall dimensions of a device after insertion in the middle ear, e.g., by swelling, uncoiling, unrolling, unfolding, splaying, untying, and so on. As a result of expansion, a preferred device having dimensions that make it insertable through a myringotomy-type incision is able to be retained in the area of the middle ear by contact between the device and the walls of the middle ear.

Suitable shapes include coiled sheets, coiled filaments, bundles of filaments or fibers (e.g., soft and pliable fibers having a large aspect ratio), and beads spaced along a filament or bundle of filaments. It is estimated that as much as 10 mg of support material can be inserted into the average adult middle ear in this manner.

The device of the present invention is preferably held in place in the middle ear by virtue of contact between the expanded device and the walls of the middle ear. In an alternative embodiment however, instead of or in addition to such contact, the device can also be held in place by providing it in a form attached to another structure or device, e.g., the device can be integrally molded with or attached to a myringotomy tube itself, and thereby anchored in place within the middle ear.

A preferred shape for a device of the present invention is that of a permeable membrane, e.g., a perforated sheet or porous web, that can be rolled into and retained in a generally cylindrical form that can be inserted into the middle ear. Once in the middle ear the material can expand by unrolling in order to form a larger cylinder, the exterior surface of which substantially contacts the walls of the middle ear.

Based on the average dimensions of the middle ear of adults, a particularly preferred support is a perforated sheet on the order of about 6 to about 12 mm wide by about 6 to about 15 mm long, and is about 0.02 to about 0.08 mm thick. The support can be rolled along its shorter axis in order to provide a cylinder having an insertable circumference of on the order of about 5 mm, and preferably about 3 mm, or less. The word "perforated" as used herein refers to a sheet that has sufficient holes penetrating its surface in order to substantially increase the passage of air and water transversely through it.

An example of a particularly preferred support is a perforated sheet of polylactic acid that is on the order of about 1 cm wide by about 1 cm long and about 0.04 mm thick. This support can be rolled to form a tube that is about 2 mm in diameter by about 1 cm long. The number and arrangement of the perforations is optional as long as communication is maintained through the sheet. Currently preferred is a sheet having about 20 to about 50, and preferably about 30 to about 40 holes per holes per square centimeter, wherein the holes are preferably of uniform size and shape, equispaced, and on the order of about 0.01 mm to about 0.1 mm in diameter.

A device is surgically inserted into the middle ear, e.g., through a small incision, and there expands in the manner described above. The term "myringotomy-type", as used herein, refers to an incision in the tympanic membrane of sufficient dimensions to insert a device of the present invention into the middle ear, e.g., an incision sufficient to insert a conventional myringotomy tube into the membrane. Typically such an incision will be between about 2 to about 5 mm in length, and preferably on the order of 3 mm in length. In use, a device can be inserted into the middle ear cavity in any suitable manner, for example using alligator forceps to place the device on the cavity wall in a position remote from the stapes.

Devices of the present invention also incorporate one or more pharmacologically active agents, preferably drugs, to be delivered to the middle and/or inner ear. The word "incorporate", as used herein, refers to any means of retaining active agent in, on, and/or by a support that provides the desired release profile.

The term "release profile", as used herein, refers to the rate, time, and amount of active agent released from the device over the period of time that the device is in place in the middle ear, e.g., as it biodegrades. While not intending to be limited by theory, release is believed to be a factor of a variety of mechanisms, including diffusion from the support by contact with mucosal wall of the middle ear, leaching of active agent from the support by contact with liquid effusions throughout the middle ear, and release of active agent in the course of the degradation of the support itself.

The stage of disease can vary, as can the presence of effusions in the ear. Effusions are believed to both accelerate the leaching of active agent and accelerate the degradation of the support, thereby releasing more active agent. Since effusions generally correspond with the presence of infection, and can persist for some time after the active infection has subsided, the effusions can provide increased active agent release from a device of the present invention at the time or times it is needed most.

Suitable means of incorporating active agent include, but are not limited to impregnating, coating, co-extruding, casting and/or covalently binding active agent to the support. Active agent can be incorporated into the support at any suitable time, e.g., before, during, or after the fabrication of the support into a shape suitable to be inserted, or even after insertion of a support into the middle ear. Preferably active agent is incorporated during the formation of the support, e.g., by casting a suspension of the agent in a dissolved polymer as described more fully below.

The amount of active agent incorporated, i.e., the loading level, is that which will provide a therapeutically effective level of active agent in the middle ear according to the desired release profile. Calculation of loading level includes a consideration of the loading capacity and the release rate of the device, and can be determined by one skilled in the appropriate art for any particular active agent or device according to the teachings provided herein. For most antibiotics, suitable loading levels are between about 0.1% and about 25%, by weight based on the weight of the final support (without retaining means such as gel), and preferred loading levels are between about 1% and about 10% by weight.

Preferably, active agent is released for on the order of months, e.g., about 1 to about 12 months and more preferably on the order of about 6 to about 8 months, after insertion. Such times correspond with the period of time that a myringotomy tube is generally kept in after it is inserted.

Suitable active agents for incorporation into a device of the present invention include those that provide the desired release profile and therapeutic effect, and that exhibit an acceptably low level of ototoxicity. Examples of active agents that can be incorporated include antibiotics such as antibacterials and antivitals, antifungals, osmotic agents such as salts or glycerine for the treatment of Meniere's Disease, fluorides or other medicaments for the treatment of otosclerosis, as well as antiinflammatory medications such as anti-prostaglandins. Since recurrent, and in many cases chronic, otitis is generally caused by *Streptococcus pneumoniae* and/or *Haemophilus influenzae*, both of which are susceptible to penicillin, penicillin and its derivatives are preferred for the treatment of otitis, and particularly preferred are ampicillin and amoxicillin.

Amino-glycoside antibiotics, although active against the most common pathogens associated with otitis are not presently preferred in that they have been shown to damage the sensory cells of the ear via transport through the natural cochlear foramen (round window membrane).

The construction and use of a preferred device of the present invention will be described with reference to the Drawing. As can be seen in FIG. 1, a preferred device (10) is shown in FIG. 1A in the shape of a flat sheet (12) having perforations (16) therein and incorporating antibiotic (not shown). In FIG. 1B device (10) is shown in the insertable shape of a rolled tube (14), having perforations (16).

A device of the present invention can be provided to the user (e.g., surgeon) either already retained in its insertable shape or retainable in such shape. For instance, a device can be provided in the form of an unrolled sheet of support material which can be then rolled by the user and held in its rolled form, e.g., with the tips of a forceps, prior to and during insertion in the middle ear. Upon removal of the forceps, the released device would be able to tend toward its original, i.e., non-retained, shape.

In an alternative and preferred approach, devices are held in their insertable shape by retaining means, e.g., a rolled tube of support material can be held in such shape with one or more ties of biodegradable suture material. Suitable retaining means include those means that; (1) are compatible with both the support and the pharmacologically active agent; (2) can be used to retain the support in its insertable shape; and (3) can be dissolved or otherwise removed once the support is inserted, in order to allow the support to expand.

Particularly preferred means for retaining a device in an insertable shape include the use of a water soluble gel. An example of a suitable gel is gelatin, preferably a gelatin such as that available from Sigma Chemical Co. as Type B, derived from bovine hide. As described more fully below, a gel can be used by physically forming (e.g., rolling) the device in its insertable shape, and retaining the device in such shape, e.g., by the use of a mold designed for such purpose. The device can then be moistened with gel solution, and the gel allowed to set, in a manner such that the set gel retains the device in the desired shape.

As illustrated in FIG. 2, the external ear canal (18), middle ear (20), and Eustachian tube (22) form essentially a continuous path that begins at the lateral portion (24) of the skull and terminates at the nasopharynx (not shown). The diameter of this path changes somewhat over its length, for instance widening near the middle ear, and constricting and convoluting near the Eustachian tube. The anterior/medial portion of the middle ear consists of a mucous membrane (26) that plays an active role in secreting effusions, transudate, and enzymes. The Eustachian tube serves to equilibrate middle ear pressure and drain debris-containing fluid from the middle ear. If the Eustachian tube becomes occluded, a negative pressure usually results, which favors the formation of transudate.

FIG. 2 also shows a preferred device (10) of the invention in rolled-up form (14) inserted in the anterior chamber of the middle ear. This represents a point in time at or very soon after insertion, before the gel has been dissolved or the device has begun to unroll. The average dimensions of the middle ear in adults is on the order of about 6 mm (posterior to anterior) by about 9 mm (lateral to medial) by about 4 mm (superior to inferior). The dimensions of the middle ear of children will be correspondingly smaller.

Figure 3:
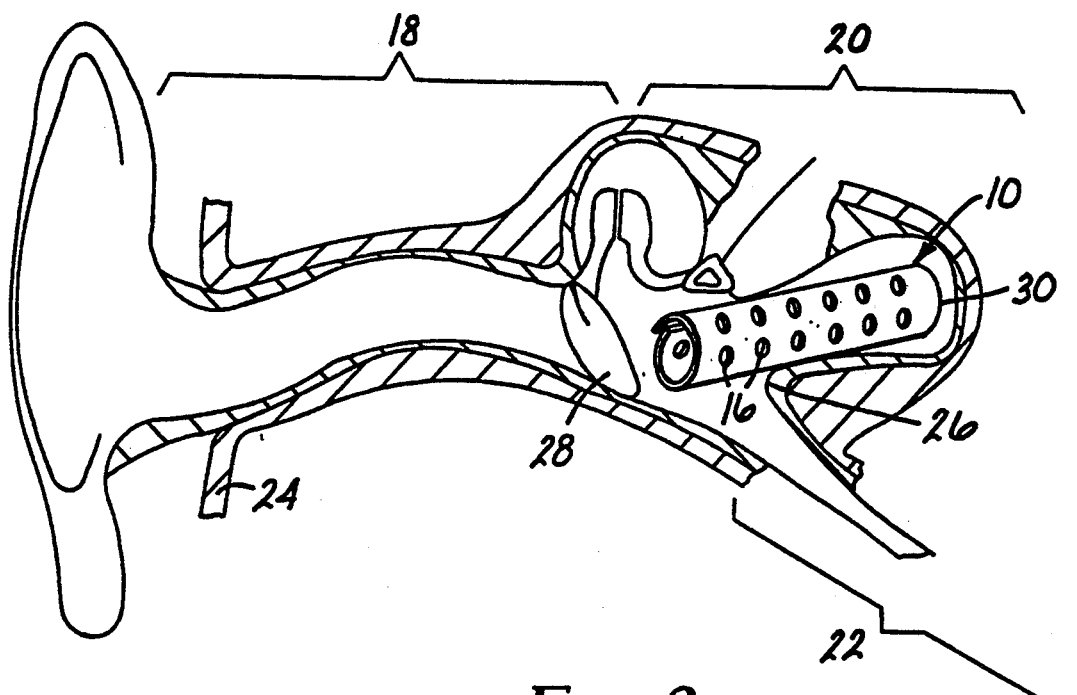
FIG. 3 illustrates the device of FIG. 2 after it has unrolled to contact the walls of the middle ear.

As illustrated in FIG. 3, device (10) shown in rolled-up form (14 in FIG. 2), is now shown in partially unrolled form (30), after insertion through an incision in tympanic membrane (28). The unrolling occurs as the fluids of the mucous membrane (26) of the middle ear dissolve the means (e.g., gel, not shown) retaining the device in its insertable form. The device is then free to unroll, and it does so until it contacts the walls of the anterior chamber where it has been placed. Perforations (16) perform at least two functions. They allow the mucous fluids, or the effusions in the event of infection, greater ease of access to the device, thus allowing enhanced access to the active agent; and they allow air and fluids to more easily pass through the inserted device.

The device of the present invention is preferably placed and used in the middle ear in a position and manner in which it is unlikely to interfere with the auditory ossicles.

Further aspects of the invention will be apparent from the following non-limiting examples.

EXAMPLES

Example 1

Preparation of Polylactic Acid Support Incorporating Antibiotic

Poly-L-lactic acid ("PLA", 4.4 g, from Birmingham Polymers Inc., Birmingham, Ala.) was dissolved in dichloromethane (100 ml). Powdered ampicillin (0.6 g, from Sigma Chemical Co., St. Louis, Mo.) was added and mixed to form a homogeneous suspension. Most of the solvent was allowed to evaporate, giving a pourable viscous suspension. This suspension was coated onto a flat Teflon ™ surface (20×40 cm). The remaining solvent was removed by evaporation in a laminar flow hood, leaving a film-like device that appeared translucent and was flexible enough to be rolled onto itself without undue force or cracking, yet was strong and stiff enough to tend towards and retain its initial flat shape. The device, about 5 microns (2 mil) in thickness, is identified below as polylactic acid loaded with 1% (by weight) of ampicillin. This device was cut into pieces 1 cm×1 cm in size.

In generally the same manner as that described above, devices incorporating PLA plasticized with triethyl citrate ("TEC") were also prepared in order to increase the pliability of the devices. TEC was used at a level of 10% by weight based on the weight of the PLA, i.e., 4.0 g PLA with 0.4 g reagent grade TEC (Aldrich Chemical Co.).

In vitro extraction of drug from these devices was evaluated as follows:

Devices were placed in 5 ml of 0.9% saline solution for 24 hours at 37° C. The saline solution was replaced with another 5 ml of saline solution, and the sample further incubated for an additional 24 hour period.

Drug levels in the saline extracts were determined using a zone of inhibition assay against *Sarcina lutea* according to the method of 21 CFR, Part 436.100, Subpart D, Microbiological Assay Methods, the disclosure of which is incorporated herein by reference, and are reported below in TABLE 1.

TABLE 1

| Results of in vitro Extraction (μg of drug released into 5 ml saline) | | |
|---|---|---|
| Drug | 0–24 hrs | 24–48 hrs |
| 0.1% amoxicillin | 1.6 | * |
| " | 2.5 | 0.4 |
| 1% amoxicillin | 24.0 | 3.5 |
| " | 19.0 | 3.0 |
| 1% ampicillin/10% TEC | 2.5 | 1.4 |
| " | 2.6 | 3.8 |
| " | 0.8 | 1.5 |

*too low to determine

As can be seen in TABLE 1, during the first 24 hours ampicillin was extractable from each of the devices in measurable concentrations. During the next 24 hours drug was extractable from all but one of the devices. The plasticized (i.e., TEC-containing) device appeared to result in initially lower but perhaps more prolonged release of the antibiotic than the unplasticized film.

Example 2

In Vivo Efficacy

Devices of PLA plasticized with 10% TEC and containing 1% ampicillin were prepared in 1×1 cm pieces as described above in EXAMPLE 1 and perforated with a custom made hole punching tool (approximately 36 equally spaced holes/cm$^2$, each about 0.05 mm diameter). The devices were sterilized with ethylene oxide before use and then surgically implanted in the middle ear cavity of chinchillas. For otological testing, the chinchilla ear is widely accepted as a good model for the human ear.

A titration study had earlier been performed in order to determine the minimum number of *S. pneumoniae* organisms that could be instilled into the middle ear of the chinchilla that would produce a severe infection if left untreated, but that would not endanger the systemic health of the animal. Various numbers of colony forming units ("CFU"), ranging from $0.5 \times 10^4$ to $0.5 \times 10^2$ were instilled in a volume of 0.5 cc by trans bulla injection. After 3 days the animals were sacrificed and examined. It was determined that one half of the animals receiving the $0.5 \times 10^4$ concentration survived, as did all of the animals at the lower concentrations. Each surviving animal had greater than $10^7$ CFU per ml in middle ear effusions. Unless otherwise indicated, all inoculations referred to below were performed using $0.5 \times 10^2$ CFU in 0.5 cc.

There were two treatment groups of four animals each, described as follows:

1. A PLA/TEC device (retained in a rolled shape for insertion by a forceps) containing 1% ampicillin (i.e., containing about 0.2 mg drug) as described above was implanted in the anterior bulla chamber overlying the cochlea and Eustachian tube opening. Each animal was inoculated at the time of surgery in the middle ear with 50 CFU *S. pneumoniae* in 0.5 cc, introduced liberally throughout the middle ear.

2. Control animals were inoculated with bacteria after implanting PLA/TEC films containing no drug.

Two days later the effusions were withdrawn and analyzed to determine the level of bacteria.

Results (reported as colony forming units—CFU/ml):

Group 1: All four animals had sterile effusions (<100 CFU/ml)

Group 2: All four animals had >$10^7$ CFU/ml.

As a result, it can be seen that infection over the short term was prevented using the device of the present invention. Since the bacterial inoculum was inoculated in a manner that covered a substantial area of the middle ear, it appears that the drug provided by the device was effective throughout the middle ear, e.g., by actual contact, diffusion, and the like. Lastly it is apparent that the support alone, i.e., without drug, was not effective in preventing the course of infection.

Example 3

Comparison of Efficacy of Device Containing Ampicillin with that of Topical Application of the Same Drug Devices of PLA plasticized with 10% TEC, each loaded with 0.2 mg of ampicillin, made by the process of EXAMPLE 1, were tested for efficacy against *S. pneumoniae* in the chinchilla anterior bulla chamber. The devices were surgically implanted (retained in a rolled shape by a forceps) in each of 5 test subjects and, during the same surgical procedure, the anterior bulla chamber of each subject was inoculated with 50 CFU of *S. pneumoniae* in 0.5 ml, introduced liberally throughout the middle ear, as in EXAMPLE 2. Three days after implantation the test animals were sacrificed and their middle ear effusions were tested for bacteria. All cultures were sterile.

Concurrently, five control subjects had their anterior bulla chambers surgically accessed. Each was inoculated with 50 CFU of *S. pneumoniae* as above, and in addition 0.2 mg of ampicillin was also injected topically into the anterior bulla chamber in 0.1 ml of aqueous suspension. Under these conditions, in the chinchilla, the antibiotic solution appeared to diffuse to all chambers, i.e., the medial, posterior, and lateral chambers. Three days later, all cultures were sterile.

In addition, 5 further control subjects also received 50 CFU of *S. pneumoniae* and a topical dose of 2.0 mg of ampicillin, all similarly introduced at surgery into the anterior bulla chamber. Three days later, all cultures were sterile.

These results indicate that the device of the present invention was at least as effective over the short term as direct topical application of either 0.2 or 2.0 mg ampicillin.

Example 4

Comparison of the Efficacy of the Device with Other Dosing Methods When Infection Occurs at a Significant Time After Dosing The materials, surgical procedures, and testing methods were the same as those used in EXAMPLE 2. However, the bacteria were injected into the anterior bulla chamber one week after insertion of a device, as opposed to concurrently with insertion.

Four groups, each having 5 test subjects, were used:

Group 1. A PLA/TEC device, loaded with 0.2 mg of ampicillin, was surgically implanted in the anterior bulla chamber of each subject on Day 1 of the procedure. On Day 7, 50 CFU of S. pneumoniae were administered.

Group 2. On Day 1 each subject was treated with 0.2 mg topical ampicillin, using the surgical procedure of the preceding EXAMPLES. On Day 7, 50 CFU of S. pneumoniae were administered similarly.

Group 3. On Day 1 each subject was treated with 2.0 mg topical ampicillin similarly. On Day 7, 50 CFU of S. pneumoniae were administered similarly.

Group 4. This group was treated with prophylactic antibiotic by the intramuscular injection of ampicillin at a dosage of 2.5 mg/kg daily for 6 days. On Day 7, 50 CFU of S. pneumoniae were administered to the anterior bulla chamber of the surgical technique of the previous EXAMPLES.

A fifth group of three subjects was used as a control:

Group 5. This group was treated only with the 50 CFU of S. pneumoniae, on Day 7 of the procedure.

On Day 10 (i.e., three days after the administration of the bacteria into the anterior bulla chamber of each subject) all animals were sacrificed and the middle ear fluid of each was cultured and tested for S. pneumoniae.

The following results were obtained:

| Group No. | Log No. of Strep. P. counted |
|---|---|
| 1. (PLA/TEC Device) | 0  0  0  0  0* |
| 2. (0.2 mg topical drug) | All subjects had high counts. |
| 3. (2.0 mg topical drug) | 0  0  0  6.3  6.4 |
| 4. (Systemic prophylaxis) | 3.4  3.1  2.3  2.3  2.0 |
| 5. (Untreated controls) | 6.5  6.5  6.5  ND  ND |

(Note: "ND" indicates no data, since only three untreated controls were used)
*Note:
One of the treated subjects in this experiment was found to have a log bacterial count of 2.6, which was found not to be due to S. pneumoniae. It is assumed that this was caused by an opportunistic strain of bacteria of unknown origin which was not susceptible to ampicillin.

The results of these in vivo experiments demonstrate the effectiveness of a middle ear drug delivery device in the prevention of otitis media caused by S. pneumoniae. The results from Group 1 demonstrate the ability of the device to maintain prophylaxis in the middle ear for a period of 7 days. In contrast, free drug delivered directly into the middle ear (Groups 2 & 3) demonstrated that even a high dose of drug was not always able to prevent infection in the middle ear when inoculation was 7 days post-treatment. The failure of a high dose of topically applied antibiotic probably reflects the capability of the middle ear mucosa to clear the drug from the middle ear.

Another observation made of the data (Group 4) is that systemic prophylaxis using antibiotics failed to produce sterile effusions. This observation is in agreement with clinical observations where patients so treated rarely develop clinical symptoms. However sustained levels of bacteria (or low levels of infections) can persist in the effusions and continue to cause long term damage to middle and inner ear structures. Note that 100 CFU/ml is used as an indication of sterility. Although patients can have concentrations far higher than 100 CFU/ml without showing any clinical symptoms of infection, it is believed that sustained subclinical infections can cause long-term damage to middle and inner ear structures.

Example 5

Demonstration of the Efficacy of the Devices to Cure Consecutive Infections

The materials, surgical procedures and testing methods were the same as those used in EXAMPLE 2.

On Day 1 five test subjects were each implanted with a PLA/TEC device loaded with 0.2 mg of ampicillin. Fifty CFU of S. pneumoniae were administered during the same surgical procedure.

On Day 7 a second 50 CFU of S. pneumoniae was administered.

Concurrently two control animals without a device were similarly treated with two administrations of 50 CFU of S. pneumoniae, 7 days apart.

On Day 10 all animals were sacrificed and the middle ear fluid of each was cultured and tested for S. pneumoniae.

The middle ear fluid of every test animal was sterile. The middle ear fluid of every control animal exhibited massive infection.

Example 6

Demonstration of the Ability of Devices of the Invention to Deliver Medication over a Prolonged Period Devices of EXAMPLE 1, with and without TEC and incorporating ampicillin (10% by weight) were subjected to an accelerated in vitro aging test by the following procedure:

Three samples of each device were tested. Each was separately placed in 5 ml of PBS solution (phosphate buffered saline, pH 7) in a closed vial, and the samples were aged in an incubator at 37° C. The PBS solutions were tested for ampicillin periodically until a total of 92 days aging had been achieved. Twenty-four hours before each test, the liquid in each vial was removed and replaced with 5 ml of fresh PBS. On the test day, the ampicillin concentration in the (fresh) liquid was determined by the zone of inhibition assay of EXAMPLE 1.

The results were:

| DAY | WITHOUT PLASTICIZER DRUG CONCN. (μg/ml) | WITH PLASTICIZER DRUG CONCN. (μg/ml) |
|---|---|---|
| 1 | 0.15 ± 0.03 | 0.13 ± 0.10 |
| 8 | 0.09 ± 0.07 | 0.13 ± 0.09 |
| 15 | 0.08 ± 0.06 | 0.06 ± 0.02 |
| 23 | 0.27 ± 0.06 | 0.28 ± 0.05 |
| 29 | 0.64 ± 0.46 | 0.49 ± 0.17 |
| 36 | 0.07 ± 0.01 | 0.34 ± 0.16 |
| 43 | 0.24 ± 0.09 | 0.17 ± 0.16 |
| 50 | 0.21 ± 0.16 | 0.19 ± 0.06 |
| 64 | 0.07 ± 0.02 | 0.20 ± 0.11 |

-continued

| DAY | WITHOUT PLASTICIZER DRUG CONCN. (µg/ml) | WITH PLASTICIZER DRUG CONCN. (µg/ml) |
|---|---|---|
| 71 | 0.04 ± 0.01 | 0.09 ± 0.04 |
| 78 | 0.17 ± 0.15 | 0.08 ± 0.05 |
| 85 | 0.20 ± 0.08 | 0.12 ± 0.08 |
| 92 | 0.20 ± 0.21 | 0.11 ± 0.07 |

The results of this accelerated aging experiment demonstrate the ability of the devices to continue to release ampicillin into an isotonic aqueous medium at physiological temperature for a period of at least about three months, indicating that devices of the present invention would be capable of releasing ampicillin to an infected middle ear for at least three months when the ear contains effusions, such as during active periods of infection, and for longer still in an ear only occasionally infected.

Example 7

In Vivo Unrolling of Support Material Retained by Gel

The ability of gelatin to retain a suitable support material in an insertable shape and then be dissolved away in vivo, allowing the support to unroll in situ was evaluated. A support material useful in a device of the invention was prepared using a polyesteramide film prepared as described in Example 17 of U.S. Pat. No. 4,343,931. A piece (approx. 1 cm × 1 cm) was rolled to a diameter of about 3 mm, and placed within a mold designed to maintain the material in its rolled configuration. A solution of 2% (by weight) gelatin (Sigma) was injected into the mold in a manner that substantially bathed the material. The gelatin solution was allowed to gel by placing the mold at 4° C. overnight, thereby retaining the material in its rolled form.

The rolled, retained support material was surgically placed through a myringotomy-type incision into the middle ear of a chinchilla. One hour later, the animal was sacrificed and the temporal bone removed to expose the middle ear. It was evident that the gelatin had dissolved away in vivo, in contact with the moist mucosal membrane of the middle ear, allowing the support material to partially unroll and be held in place by the walls of the middle ear.

We claim:

1. A method of treating otitis media comprising inserting into the middle ear a biodegradable, substantially permeable support device incorporating a therapeutically effective releasable amount of at least one pharmacologically active agent selected from the group consisting of antibacterials, antivirals, antifungals, fluorides, salts, glycerine and antiinflammatory medications, the characteristics of the device being that (1) the device is a cylindrical sheet or coiled filament retained or retainable in an insertable shape of initial dimensions that allow it to be surgically inserted into the middle ear; (2) upon insertion into the middle ear, the device is capable of expanding towards its original shape in order to provide a surface that substantially contacts the walls of the middle ear without substantially occluding the middle ear space; and (3) once expanded, the device is capable of providing extended release of the active agent to the middle ear.

2. The method according to claim 1 wherein the insertable shape is a cylindrical sheet having initial dimensions of a diameter of less than about 2 mm, a length of about 1 cm, and wherein the sheet unrolls in the middle ear to form a tube of on the order of 1 cm circumference and about 0.4 cm to about 0.6 cm diameter.

3. The method according to claim 1 wherein the support device biodegrades within about 2-18 months.

4. A method of delivering pharmacologically active agents to the middle ear comprising inserting into the middle ear a biodegradable, substantially permeable support device incorporating a therapeutically effective releasable amount of at least one pharmacologically active agent, the characteristics of the device being such that (1) the device is provided retained or retainable in an insertable shape of initial dimensions that allow it to be surgically inserted into the middle ear; (2) upon insertion into the middle ear, the device is capable of expanding towards its original shape in order to provide a surface that substantially contacts the walls of the middle ear without substantially occluding the middle ear space; and (3) once expanded, the device is capable of providing extended release of the active agent to the middle ear;

wherein the insertable shape is a cylindrical sheet having initial dimensions of a diameter of less than about 2 mm, a length of about 1 cm, and wherein the sheet unrolls in the middle ear to form a tube of on the order of 1 cm circumference and about 0.4 cm to about 0.6 cm diameter;

wherein the support is made of a material selected from the group consisting of polyesteramides, polyglycolic acid, polylactic acid, copolymers of glycolide and lactide, polyvinyl alcohol, copolymers of polyethylene oxide and polylactic acid, and chemically modified coilagent compounds; and wherein the pharmacologically active agent is selected from the group consisting of antibacterials, antivirals, antifungals, osmotic agents, fluorides and antiinflammatory medications.

5. A device to deliver pharmacologically active agents to the middle ear consisting essentially of biodegradable, substantially permeable support, incorporating a therapeutically effective releasable amount of at least one pharmacologically active agent selected from the group consisting of antibacterials, antivirals, antifungals, fluorides, salts, glycerine and antiinflammatory medications, the characteristics of the device being that (1) the device is retained or retainable as coiled filament having initial dimensions that allow it to be surgically inserted into the middle ear; (2) upon insertion into the middle ear, the device is capable of expanding towards its original shape in order to provide a surface that substantially contacts the walls of the middle ear without substantially occluding the middle ear space; (3) once expanded, the device is capable of providing extended release of the active agent to the middle ear; and (4) the support degrades within about 2-18 months when inserted into the middle ear.

* * * * *

UNITED STATES PATENT AND TRADEMARK OFFICE
CERTIFICATE OF CORRECTION

PATENT NO. : 5,350,580
DATED : September 27, 1994
INVENTOR(S) : David C. Muchow and Larry M. Sirvio It is certified that error appears in the above-indentified patent and that said Letters Patent is hereby corrected as shown below:

Col. 7, line 18   "antivitals" should read --antivirals--

Signed and Sealed this

Twelfth Day of September, 1995

Attest:

BRUCE LEHMAN

*Attesting Officer*     *Commissioner of Patents and Trademarks*